United States Patent
Kusukame et al.

(10) Patent No.: US 10,077,369 B2
(45) Date of Patent: Sep. 18, 2018

(54) INKJET PRINTING INK

(71) Applicant: Panasonic Intellectual Property Management Co., Ltd., Osaka (JP)

(72) Inventors: Haruka Kusukame, Nara (JP); Masayo Shinoda, Tokyo (JP); Tomoki Masuda, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/257,763

(22) Filed: Sep. 6, 2016

(65) Prior Publication Data

US 2017/0073535 A1  Mar. 16, 2017

(30) Foreign Application Priority Data

Sep. 15, 2015 (JP) ................................. 2015-182112

(51) Int. Cl.
*C09D 11/107* (2014.01)
*C09D 11/36* (2014.01)
*C09D 11/322* (2014.01)

(52) U.S. Cl.
CPC ............ *C09D 11/36* (2013.01); *C09D 11/107* (2013.01); *C09D 11/322* (2013.01)

(58) Field of Classification Search
None
See application file for complete search history.

(56) References Cited

U.S. PATENT DOCUMENTS

| 2005/0036021 A1* | 2/2005 | Ito .......................... | C09D 11/40 347/100 |
| 2011/0263752 A1* | 10/2011 | Hiraishi ............... | C09D 11/322 523/310 |
| 2013/0127953 A1* | 5/2013 | Furukawa ............ | C09D 11/107 347/68 |
| 2015/0109365 A1* | 4/2015 | Taya .................... | C09D 11/033 347/20 |
| 2016/0130453 A1* | 5/2016 | Eguchi ................. | C09D 11/322 347/20 |

FOREIGN PATENT DOCUMENTS

| EP | 3006519 A1 | 4/2016 | |
| JP | 63-063363 | 3/1988 | |
| JP | 3-157313 | 7/1991 | |
| JP | 9-302294 | 11/1997 | |
| WO | WO-2014196578 A1 * | 12/2014 | ........... C09D 11/322 |

OTHER PUBLICATIONS

The Extended European Search Report issued with respect to application No. 16185795.8, dated Jan. 3, 2017.

* cited by examiner

*Primary Examiner* — Richard A Huhn
(74) *Attorney, Agent, or Firm* — Greenblum & Bernstein, P.L.C.

(57) ABSTRACT

An inkjet printing ink according to the present disclosure contains a pigment, acrylic particles, an alcohol, and water. The alcohol contains at least a trihydric alcohol. A ratio of an amount of the alcohol to a whole mass of the inkjet printing ink is 30% by mass or less. A ratio of an amount of the acrylic particles to a mass of the pigment is 5% by mass to 100% by mass. Further, the inkjet printing ink has negative skin irritation.

10 Claims, 4 Drawing Sheets

INKJET PRINTING INK

BACKGROUND

1. Technical Field

The present disclosure relates to an inkjet printing ink which has excellent jetting stability and is safe for living bodies.

2. Description of the Related Art

Inkjet printers have dramatically come into widespread use because of their advantageous properties including low noise and low running cost, and color printers which enable the printing on plain paper have also been provided increasingly on the market. However, in inkjet printers, it is very difficult to satisfy all of properties required for the inkjet printers, including color reproducibility in images, good image drying characteristics, prevention of blurring of characters or blurring of boundaries between colors and jetting stability. Therefore, the type of an ink to be used is selected on the basis of intended use or properties having higher priority.

For example, aqueous inks containing water as a main component, and also containing a coloring agent such as a dye and a pigment and a wetting agent such as glycerin are generally known. However, such aqueous inks may be insufficient with respect to image fixability depending on the types of substrates used.

In recent years, inks containing an organic solvent and therefore having high drying characteristics have also been provided. However, inks containing an organic solvent may be poor in safety for living bodies and the environment. Therefore, such inks are not suitable for practical applications for which safety for living bodies is required.

Meanwhile, for the purpose of diversifying the types of printable substrates, inks containing an ultraviolet (UV)-curable resin that can be cured by the irradiation with UV rays have been provided. However, in inks containing a reactive compound as mentioned above, there is a possibility that an unreacted compound remains, and the unreacted compound may affect living bodies and others. Therefore, the UV-curable inks are not suitable for practical application for which safety for living bodies is required, either.

In these situations, as inks having high safety for living bodies, edible inks have been proposed. For example, edible screen printing inks, each of which contains water, an alcohol, a surfactant, an edible insoluble inorganic micropowder having concealing properties, a thickening agent, a resin, an edible polymeric substance and the like, have been proposed (see, for example, PTL 1). Card-type cosmetics and the like, each of which is produced by pouring a suspension containing a cosmetic-use powdery material and an oily substance dispersed in a water-soluble binder, by screen printing have also been proposed (see, for example, PTL 2). However, these inks and suspensions have formulations suitable for a screen printing technique, and therefore it is difficult to use the inks as inkjet printing inks without any modification. Meanwhile, inks containing an edible dye have been reported as edible inks that can be used for inkjet printing (PTL 3).

However, in edible inks as disclosed in PTL 3, there is a problem that coloring materials are often deteriorated by the action of light or oxygen, and therefore the permanency of images formed from the inks is poor. Therefore, the fact is that an inkjet printing ink having all of requirements of safety for living bodies, permanency and jetting stability is not produced yet.

CITATION LIST

Patent Literatures

PTL 1: Unexamined Japanese Patent Publication No. 63-63363

PTL 2: Unexamined Japanese Patent Publication No. H03-157313

PTL 3: Unexamined Japanese Patent Publication No. H09-302294

SUMMARY

Thus, a non-limiting exemplary embodiment of the present disclosure provides an inkjet printing ink, which is highly safe for living bodies, can be ejected from an inkjet printer stably, and can provide an image having high permanency.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

The present inventors have made extensive and intensive studies. As a result, it is found that an inkjet printing ink containing a pigment, acrylic particles, an alcohol, and water can be ejected from an inkjet printer stably when the content of the alcohol is equal to or smaller than a specified amount, and at least a trihydric alcohol is contained in the alcohol. In this regard, it is also found that the fixability of an image formed from the ink can be improved when the amount of the acrylic particles relative to the amount of the pigment falls within a specified range. Furthermore, it is also found that an ink having both high permanency and safety for living bodies can be provided when the ink mainly contains a pigment, acrylic particles, an alcohol, and water. These findings lead to the accomplishment of the present application.

In one general aspect, the techniques disclosed here feature: an inkjet printing ink containing a pigment, acrylic particles, an alcohol, and water, wherein the alcohol contains a trihydric alcohol, a ratio of an amount of the alcohol to a whole mass of the inkjet printing ink is 30% by mass or less, a ratio of an amount of the acrylic particles to a mass of the pigment is 5% by mass to 100% by mass, and the inkjet printing ink has negative skin irritation.

The inkjet printing ink according to the present disclosure is highly safe for living bodies, can be ejected from an inkjet printer stably, and can provide an image having high permanency and fixability. Therefore, the inkjet printing ink can form a high definition image on various types of substrates including plain paper, dedicated recording paper, a plastic material and a cloth.

DETAILED DESCRIPTION

The inkjet printing ink according to the present disclosure contains at least a pigment, acrylic particles, an alcohol, and water. The inkjet printing ink may additionally contain other components, if necessary.

The inkjet printing ink according to the present disclosure has negative skin irritation (non-skin irritation). In other words, the inkjet printing ink is highly safe for living bodies. Therefore, the inkjet printing ink can be used in various use applications. For example, the inkjet printing ink can be applied to substrates that are used in contact with skin or the like. The wording "have (has, having) negative skin irritation" as used herein means that, when a test, which is an alternative method to a skin irritation test, is carried out on a three-dimensional skin model, the survival rate of cells in the model is more than 50%. The alternative method to a skin irritation test is carried out using a 5% sodium dodecyl sulfate (SDS) solution as an irritation control, and using phosphate buffered saline (PBS) as a negative control. In the method, the ink is exposed to the three-dimensional skin model for 18 hours, and subsequently the survival rate of cells in the model is evaluated by a 3-(4,5-dimethyl-2-thiazolyl)-2,5-diphenyl-2H-tetrazolium bromide (MTT) test.

In the present disclosure, as one example of the technique for making the skin irritation of the inkjet printing ink negative, a technique can be mentioned in which all of the components to be contained in the inkjet printing ink are selected from components included in the List of Cosmetics Ingredients stipulated in the Pharmaceutical Affairs Law.

The inkjet printing ink according to the present disclosure contains at least a trihydric alcohol. In general, when the drying characteristics of an ink are unduly high, clogging or the like is likely to occur in an inkjet head of an inkjet printer. On the contrary, in the inkjet printing ink according to the present disclosure, since a trihydric alcohol is contained, the drying characteristics of the inkjet printing ink can be controlled appropriately and, as a result, the inkjet printing ink can be ejected from an inkjet printer stably.

In the inkjet printing ink, the amount of the acrylic particles relative to the amount of the pigment falls within a specified range. Therefore, in an image formed from the inkjet printing ink, the acrylic particles act as a binder for binding the pigment to a substrate. Consequently, the fixability of the image is improved greatly, and the water resistance of the image is also improved. In the inkjet printing ink according to the present disclosure, the component for coloring the ink is a pigment, and therefore the deterioration of an image by the action of light or oxygen rarely occurs and the permanency of the image is improved.

Hereinbelow, the components contained in the inkjet printing ink will be described.

(Pigment)

The pigment to be contained in the inkjet printing ink according to the present disclosure is not limited particularly, and is preferably a component selected from components included in the List of Cosmetics Ingredients stipulated in the Pharmaceutical Affairs Law as mentioned above, from the viewpoint of skin irritation. The pigment may be any one selected from known inorganic pigments and known organic pigments. The pigment can be selected appropriately depending on the color required as the color of a substrate or the appearance of the substrate. Examples of the pigment include a color pigment for coloring the inkjet printing ink as well as a pearlescent pigment for imparting gloss to an image. In the inkjet printing ink, only one type of pigment may be contained, or two or more types of pigments may be contained.

The pigment may be a known pigment that is applicable to a cosmetic or the like. Specific examples of the pigment include inorganic red pigments such as iron oxide, iron hydroxide and iron titanate; inorganic brown pigments such as γ-iron oxide; inorganic yellow pigments such as yellow iron oxide and ocher; inorganic black pigments such as black iron oxide and carbon black; inorganic white pigments such as titanium oxide; inorganic violet pigments such as manganese violet and cobalt violet; inorganic green pigments such as chromium hydroxide, chromium oxide, cobalt oxide and cobalt titanate; inorganic blue pigments such as iron blue (ferric ferrocyanide) and ultramarine blue; a laked product of a tar pigment; a laked product of a natural pigment; and a synthetic resin powder produced by forming the aforementioned powders into a complex.

Specific examples of the pearlescent pigment include titanium oxide-coated isinglass, titanium oxide-coated mica, bismuth oxychloride, titanium oxide-coated bismuth oxychloride, titanium oxide-coated talc, fish scale foil and titanium oxide-coated colored isinglass.

The shape of the pigment is not particularly limited and may be a spherical shape, a needle-like shape or the like. It is preferred that the pigment has such a shape that the median value (median diameter (D50)) of an integral value of the particle size distribution of the pigment as determined by a laser diffraction method is preferably 0.001 µm to 0.6 µm, more preferably 0.01 µm to 0.3 µm. When the median diameter (D50) of the particle size distribution of the pigment falls within the aforementioned range, it becomes possible to eject the inkjet printing ink from a head of an inkjet printer stably.

The amount of the pigment to be contained in the inkjet printing ink is 40% by mass or less, more preferably 3% by mass to 10% by mass, relative to the whole mass of the inkjet printing ink. When the amount of the pigment is 3% by mass or more, a substrate can be colored sufficiently, and the substrate is likely to be imparted with gloss. If the amount of the pigment is excessive, clogging or the like in a head of an inkjet printer is likely to occur, or the pigment may be agglomerated during storage of the inkjet printing ink. In this case, however, when the amount of the pigment is 40% by mass or less, the agglomeration of the pigment and the like hardly occurs, and the inkjet printing ink can be ejected from an inkjet printer stably.

(Acrylic Particles)

The acrylic particles act as a binder between the pigment and a substrate. The acrylic particles are not particularly limited, as long as the acrylic particles are formed from an acrylic resin having negative skin irritation and can be dispersed stably and uniformly in water or the alcohol. The component for the acrylic particles is preferably selected from components included in the List of Cosmetics Ingredients stipulated in the Pharmaceutical Affairs Law, and the acrylic particles may be particles of a known acrylic resin which have been used in cosmetics and the like.

Specific examples of the component for the acrylic particles include a homopolymer of an acrylic monomer, a copolymer of at least two types of acrylic monomers, and a copolymer of an acrylic monomer and a different monomer. In the inkjet printing ink, only one type of acrylic particles may be contained or two or more types of acrylic particles may be contained.

Specific examples of the acrylic monomer include acrylic acid, methyl acrylate, ethyl acrylate, acrylic acid amide, n-propyl acrylate, n-butyl acrylate, isobutyl acrylate, octyl acrylate, 2-ethylhexyl acrylate, N,N-dimethylaminoethyl acrylate, acrylonitrile, methacrylic acid, ethyl methacrylate, methacrylic acid amide, n-propyl methacrylate, n-butyl methacrylate, isobutyl methacrylate, 2-ethylhexyl methacrylate, octyl methacrylate, hydroxyethyl methacrylate and N,N-dimethylaminoethyl methacrylate.

Specific examples of the monomer copolymerizable with the acrylic monomer include styrene, vinyl acetate, a silicone macromer, a fluorinated monomer and an alkoxysilane unsaturated monomer.

When the aforementioned acrylic particles are used, it is likely that better fixability of an image formed from the inkjet printing ink can be achieved, and good permanency of the image can also be achieved.

In this regard, the amount of the acrylic particles to be contained in the inkjet printing ink is 0.5 parts by mass to 10 parts by mass, more preferably 1.5 parts by mass to 5.7 parts by mass, relative to 10 parts by mass of the aforementioned pigment. As mentioned above, when the amount of the acrylic particles relative to the amount of the pigment falls within the aforementioned range, the fixability of an image formed from the inkjet printing ink is improved. If the amount of the acrylic particles is excessive, the viscosity of the inkjet printing ink tends to increase excessively. In addition, if the amount of the acrylic particles is excessive, clogging in an inkjet head and the like may occur during printing. On the contrary, when the amount of the acrylic particles falls within the aforementioned range, the viscosity of the inkjet printing ink can be adjusted within a desired range, and the inkjet printing ink can be ejected from an inkjet printer stably.

In the preparation of the inkjet printing ink, the acrylic particles are generally mixed, in a state of being dispersed in a dispersion medium (in a state of an emulsion), with the pigment, water, the alcohol and the like. The dispersion medium to be used in the mixing is preferably a solvent having negative skin irritation, and is preferably the below-mentioned alcohol or water.

(Alcohol)

The alcohol acts as an ink dryness preventing agent and also acts as a solvent in the inkjet printing ink. The alcohol is absorbed into a substrate or vaporized after being dropped onto a substrate for the inkjet printing ink.

As mentioned above, the alcohol contains a trihydric alcohol. When the inkjet printing ink contains a trihydric alcohol, it becomes possible to prevent the vaporization of water or the alcohol in an inkjet printer. As a result, clogging in an inkjet head and the like hardly occurs, and an image can be formed stably. Furthermore, the viscosity of the inkjet printing ink can be maintained at a constant level, and therefore it becomes possible to form an image stably.

The trihydric alcohol is not particularly limited, as long as the trihydric alcohol is not irritable to skin. The trihydric alcohol is preferably glycerin. Glycerin is highly safe for living bodies. When the inkjet printing ink contains glycerin, the agglomeration of the pigment is likely to be prevented, and the ink thickening or the like hardly occurs even when the inkjet printing ink is stored for a long period.

In this regard, the inkjet printing ink may contain a dihydric alcohol or a monohydric alcohol. Specific examples of the dihydric alcohol include diethylene glycol, propylene glycol, 1,3-propanediol, butylene glycol and hexanediol. Specific examples of the monohydric alcohol include alcohols having 1 to 4 carbon atoms, such as ethanol, propanol, isopropanol and butyl alcohol. Among these alcohols, a dihydric alcohol is preferred, and propylene glycol is particularly preferred. A dihydric alcohol has a lower viscosity and a lower surface tension than those of water and glycerin. Therefore, when the inkjet printing ink contains a dihydric alcohol, the wettability of the inkjet printing ink on a substrate is good, and non-uniformity in an image formed from the inkjet printing ink is hardly developed.

In the present disclosure, the alcohol is contained in an amount of 30% by mass or less in the inkjet printing ink. The amount of the alcohol is preferably 10% by mass to 30% by mass, more preferably 20% by mass to 30% by mass. If the amount of the alcohol in the inkjet printing ink is excessive, the pigment or the like tends to be agglomerated. When the amount of the alcohol is 30% by mass or less, the agglomeration of the pigment and the like hardly occurs, and it becomes possible to eject the inkjet printing ink from an inkjet printer stably.

The amount of the trihydric alcohol is preferably 10% by mass to 30% by mass, more preferably 10% by mass to 20% by mass, relative to the whole amount of the inkjet printing ink. That is, it is particularly preferred for the inkjet printing ink to contain glycerin in an amount of 10% by mass to 30% by mass. When the amount of the trihydric alcohol falls within the aforementioned range, the volatility of the alcohol and water can be controlled appropriately, and therefore it becomes possible to eject the inkjet printing ink from an inkjet printer stably.

The amount of the dihydric alcohol is preferably 10% by mass to 30% by mass, more preferably 10% by mass to 20% by mass, relative to the whole amount of the inkjet printing ink. When the amount of the dihydric alcohol falls within the aforementioned range, the viscosity of the inkjet printing ink is likely to fall within a desired range, and therefore it becomes possible to eject the inkjet printing ink from an inkjet printer stably.

(Water)

Water to be contained in the inkjet printing ink according to the present disclosure is preferably purified water. The amount of water to be contained in the inkjet printing ink can be selected appropriately depending on the viscosity of the inkjet printing ink or the like.

(Other Components)

The inkjet printing ink may contain components other than the aforementioned components, as long as the disclosed effects cannot be lost. Other components are preferably compounds having negative skin irritation. Specific examples of the aforementioned other components include a surfactant, a pH adjuster, a thickening agent, an ultraviolet absorber, an ultraviolet scattering agent, an antimicrobial and antifungal agent, a deoxidizing agent, an antioxidant agent, a preservative agent, an antifading agent, an antifoaming agent, a fragrance, and a solvent other than an alcohol or water.

(Method for Preparing Inkjet Printing Ink)

The inkjet printing ink can be prepared by fully mixing an emulsion containing the pigment and the acrylic particles, the alcohol, water and other components together with a known dispersing machine, such as a ball mill, a sand mill, a roll mill, a homomixer and an attritor.

(Physical Properties of Inkjet Printing Ink)

The viscosity of the inkjet printing ink is preferably 1 mPa·s to 20 mPa·s, more preferably 3.5 mPa·s to 8 mPa·s, at 25° C. as measured with a cone-plate type viscometer at a shear rate of 100 (1/s) or 1000 (1/s). When the viscosity of the inkjet printing ink falls within the aforementioned range, the inkjet printing ink can be ejected from and inkjet printer stably.

The pH value of the inkjet printing ink is preferably 7.0 to 9.5. When the pH value of the inkjet printing ink falls within the aforementioned range, the inkjet printing is stable in the inside of an inkjet printer. Furthermore, when the pH values falls within the aforementioned range, agglomeration of the pigment and the like hardly occurs when the inkjet printing ink is stored for a long period, and therefore the inkjet printing ink can be ejected from an inkjet printer easily.

The surface tension of the inkjet printing ink at 25° C. is preferably 32 mN/m to 46 mN/m. If the surface tension is smaller than the aforementioned range, the bleeding of ink droplets on various types of substrates is likely to occur when the inkjet printing ink is ejected from an inkjet printer onto the substrates. If the surface tension is higher than the aforementioned range, the dewetting of ink droplets is likely to occur. When the surface tension falls within the aforementioned range, the wettability of ink droplets is good during the ejection of the inkjet printing ink from an inkjet printer onto various substrates, and therefore it becomes possible to form an image having a uniform thickness. In this regard, the measurement of the surface tension can be carried out by various measurement methods, and the aforementioned values are determined by a pendant drop method that can be applied to general-purpose devices.

Furthermore, it is preferred that the median value (median diameter (D50)) of an integrated value of the particle size distribution of particles contained in the inkjet printing ink as measured by a laser diffraction method is 600 nm or less, more preferably 10 nm to 300 nm. When the median diameter of the pigment falls within the aforementioned range, it becomes possible to eject the inkjet printing ink from an inkjet printer stably. It is also preferred that the 90% value (D90) of an integrated value of the particle size distribution is 900 nm or less. When the D50 value and the D90 value respectively fall within the aforementioned ranges, it becomes possible to eject the inkjet printing ink from an inkjet printer stably.

(Printing with Inkjet Printing Ink)

The inkjet printer from which the inkjet printing ink according to the present disclosure is to be ejected is not particularly limited, and may be any known device selected from a piezo inkjet printer, a thermal inkjet printer and an electrostatic inkjet printer, and is particularly preferably a piezo element-inkjet printer. A piezo element-type inkjet printer has such an advantage that a heating procedure is not needed, unlike a thermal inkjet type one.

Meanwhile, a substrate onto which the inkjet printing ink according to the present disclosure is to be ejected is not particularly limited, and the inkjet printing ink can be applied to various known substrates including plain paper, dedicated recording paper, a plastic material and a cloth. The substrate may be composed of only one layer, or may be a laminate of two or more layers. The inkjet printing ink according to the present disclosure is negative skin irritation, and therefore the resultant printed matter is highly safe for living bodies. Consequently, the inkjet printing ink can be printed onto various sheets which are attached or closely adhered directly or indirectly onto skin for example, and each of which is made from a biocompatible material.

Specific examples of the material having biocompatibility include a polyester typified by polyglycolic acid, polylactic acid, polycaprolactone, polyethylene succinate, polyethylene terephthalate and copolymers thereof; a polyether typified by polyethylene glycol and polypropylene glycol; a polyamide typified by nylon, polyglutamic acid, polyaspartic acid and salts thereof; a polysaccharide typified by pullulan, cellulose, starch, chitin, chitosan, alginic acid, hyaluronic acid and corn starch, or a salt thereof; a silicone typified by acryl silicone and trimethylsiloxysilicic acid; an acrylate typified by an alkyl acrylate, silicone acrylate, acrylic acid amide, and copolymers thereof; polyvinyl alcohol; polyurethane; polycarbonate; a poly acid anhydride; polyethylene; and polypropylene.

Specific examples of a sheet made from a material having biocompatibility include a sheet for fixing a medical member, a taping sheet for sport applications, a skin-decorating sheet, and a cosmetic sheet.

The thickness of the substrate is not particularly limited, and can be selected appropriately depending on the type, intended use and the like of the substrate. Since the inkjet printing ink according to the present disclosure contains a pigment together with acrylic particles, the pigment can be firmly adhered easily onto a substrate surface by the action of the acrylic particles. Therefore, the inkjet printing ink of the present disclosure can also be printed on a thin film having a thickness of, for example, 10 nm to 3000 nm inclusive, more preferably 10 nm to 1000 nm inclusive.

In the formation of an image on a thin film as mentioned above, it is possible to subject a laminate, that is produced by laminating the thin film on a support material that supports the thin film, to printing, and then separate the thin film from the support material after the printing. The support material may be made from a material having high water absorption properties. When the support material has water absorbing properties, the alcohol and water can be absorbed into the support material rapidly, and only the pigment and the acrylic particles are firmly fixed onto the surface of the thin film. Consequently, the resultant image rarely undergoes bleeding and the like, and it becomes possible to form a highly fine image. Specific example of the support material having high water absorption properties include paper, a cloth, a non-woven fabric, a woven fabric, a porous layer-coated sheet, a nano-fiber sheet, and a base material formed from a water-absorbable polymer, a water-soluble polymer or the like.

EXAMPLES

Hereinbelow, the present disclosure will be described by way of examples. It should be noted that the scope of the present disclosure is not intended to be limited by the following examples.

[Materials]

The materials used in examples and comparative examples are as follows.

(Pigments)

Yellow pigment: iron oxide yellow (D50: 217 nm)
Red pigment: iron oxide red (D50: 291 nm)
White pigment: titanium oxide (D50: 103 nm)
Blue pigment: ferric ferrocyanide (D50: 159 nm)
Black pigment: carbon black (D50: 112 nm)

(Acrylic Particles)

An acrylate copolymer (Solvents)

Glycerin
1,3-Propane diol (PD)
Purified water (Other components)

A pH adjuster
A nonionic surfactant (a sucrose fatty acid ester)
An anionic surfactant (polyoxyethylenelauryl ether acetate sodium salt)
Polyvinyl alcohol
Silicon-based particles (dimethicone)

Example 1

Materials shown in Table 1 were mixed together at compounding compositions shown in Table 1 to separately prepare a yellow ink, a red ink, a white ink, a blue ink and a black ink (inkjet printing inks). In some of the examples, for the purpose of adjusting the pH value of an inkjet printing ink to a value ranging from 7.0 to 9.5, a portion of water was replaced with a pH adjuster to adjust the pH value of an ink. Therefore, in Table 1, the total amount of water and a pH adjuster is shown.

[Evaluation]

The resultant inkjet printing inks were measured with respect to skin irritation, particle size distribution and viscosity by the following methods. The ink fixability of the inkjet printing inks was also confirmed by the following method. The results are shown in Table 1.

(Skin Irritation)

The skin irritation of the prepared inks was evaluated by an alternative testing method for skin irritation test using a three-dimensional skin model. Specifically, the test was carried out using a 5% sodium dodecyl sulfate (SDS) solution as an irritation control and using phosphate buffered saline (PBS) as a negative control. As a test sample, a printed matter prepared by applying each of the prepared inks on a polyester film by inkjet printing was used. An ink-printed surface of the test sample was exposed to a skin model for 18 hours, then the skin model was washed with PBS to remove the test sample completely, then the skin model was transferred into a test culture medium containing 0.3 mg/mL of 3-(4,5-dimethyl-2-thiazolyl)-2,5-diphenyl-2H-tetrazolium bromide (MTT), and then the skin model was cultured for 3 hours. Subsequently, the skin model was immersed in acidic isopropanol for 24 hours to extract blue formazan. The absorbance of the resultant extract was measured at 550 nm with a microplate reader. The cell survival rate of each test sample was expressed in terms of a percentage in which the absorbance of a skin model exposed to the negative control was defined as 100. It was determined that a test sample had no skin irritation when the cell survival rate was more than 50%, while it was determined that a test sample had skin irritation when the cell survival rate was less than 50%.

(Particle Size Distribution)

The particle size distribution of each of the prepared inks was measured. The measurement of the particle size distribution was carried out using a particle size distribution analyzer "Microtrac UPA150" (manufactured by Nikkiso Co., Ltd.) under the conditions of a laser wavelength of 780 nm and a laser output of 3 mW. The particle size distribution was measured for a period starting from 2 weeks after the preparation of the inks to 4 weeks after the same to evaluate the time course of the change in the particle size distribution. When no change is observed, it is determined that the ink can be ejected stably from an inkjet printer. In Table 1, median values (D50) of the particle size distributions and 90% values (D90) of integrated values of the particle distributions after the elapse of 4 weeks after the preparation of the inks are shown. When a (D50) value is 600 nm or less and a (D90) value is 900 nm or less, it is determined that an ink can be printed stably with an inkjet printer.

(Viscosity)

The measurement of a viscosity of each of the prepared inks was carried out using a viscosity/viscoelasticity meter HAAKE MARS (manufactured by Thermo Fisher Scientific Inc.). Specifically, a portion (0.3 cc) of each of the inks was collected with a syringe to sample the portion in a cone plate, and the measurement was carried out at a measurement temperature of 25° C. while changing the shear rate from 0.1 (1/s) to 1000 (1/s). When the viscosity at 25° C. is 20 mPa·s or less, it is determined that the ink can be printed with an inkjet printer stably. Particularly when the viscosity is 8 mPa·s or less, it is determined that the ink can be printed very stably.

(Ink fixability)

Each of the resultant color inks was filled in an ink tank in an inkjet printer equipped with an inkjet head LB3 (manufactured by Panasonic precision Device Co., Ltd.). Subsequently, a rectangular fill pattern having a size of 15 mm×5 mm was formed on a paper filter (thickness: 270 μm), which served as a substrate, using each of the inks. The printed sheet (i.e., a printed matter) was left under an environment of room temperature or 50° C.

A polylactic acid sheet having a thickness of 200 nm was bonded to a support material composed of a paper filter. The bonding was carried out by wetting an attachment surface of the polylactic acid sheet and an attachment surface of the support material with water separately, then adhering the wetted surfaces of the sheets to each other to bond the wetted surfaces to each other, and then drying the resultant product for 12 hours or longer. On a laminated printed sheet thus produced, a rectangular fill pattern having a size of 15 mm×5 mm was formed using an inkjet printer in the same manner as mentioned above. The printed sheet (i.e., a printed matter) was left under an environment of room temperature or 50° C.

A ply of tissue paper was pressed against each of the printed patterns every several minutes. The ink fixability was evaluated on the basis of the presence or absence of ink adhesion on the tissue paper.

The criteria for the evaluation are the following four ratings:

⊙: ink adhesion disappeared within 5 minutes;
○: ink adhesion was observed within 5 minutes, but disappeared within 10 minutes;

Δ: ink adhesion was observed within 10 minutes, but disappeared within 30 minutes; and
x: ink adhesion was observed even after 30 minutes.

TABLE 1

|  | Example 1-1<br>Yellow ink | Example 1-2<br>Red ink | Example 1-3<br>White ink | Example 1-4<br>Blue ink | Example 1-5<br>Black ink |
|---|---|---|---|---|---|
| Pigment | Iron oxide yellow<br>10% by mass | Iron oxide red<br>10% by mass | Titanium oxide<br>10% by mass | Ferric ferrocyanide<br>5% by mass | Carbon black<br>5% by mass |
| Acrylic particles | 2.5% by mass | | | | |
| Alcohol | glycerin: 10% by mass<br>1,3-propanediol: 10% by mass | | | | |
| Water +<br>pH adjuster | 67.5% by mass<br>(without pH<br>adjuster) | 67.5% by mass<br>(without pH<br>adjuster) | 67.5% by mass<br>(without pH<br>adjuster) | 69.5% by mass<br>(with pH adjuster) | 69.0% by mass<br>(with pH<br>adjuster) |
| Surfactant | — | — | — | Nonionic<br>surfactant<br>3% by mass | Anionic<br>surfactant<br>3.5% by mass |
| Skin irritation | Irritation was not<br>observed | Irritation was not<br>observed | Irritation was not<br>observed | Irritation was not<br>observed | Irritation was not<br>observed |
| Particle size<br>distribution<br>(nm) | D50: 240<br>D90: 620 | D50: 292<br>D90: 707 | D50: 175<br>D90: 350 | D50: 210<br>D90: 397 | D50: 147<br>D90: 236 |
| Viscosity<br>(mPa · s) | 5.3 | 5.6 | 3.0 | 3.5 | 5.2 |
| Ink fixability — Ambient temperature (paper filter) | ⊙ | ⊙ | ⊙ | ⊙ | ⊙ |
| 50° C. (paper filter) | ⊙ | ⊙ | ⊙ | ⊙ | ⊙ |
| Ambient temperature (thin film) | ⊙ | ⊙ | ⊙ | ⊙ | ⊙ |
| 50° C. (thin film) | ⊙ | ⊙ | ⊙ | ⊙ | ⊙ |

(Results)

As shown in Table 1 above, when, in inkjet printing inks containing a pigment, acrylic particles, an alcohol, and water, the alcohol contained a trihydric alcohol, the amount of the alcohol was 30% by mass or less relative to the whole mass of each of the inks and the amount of the acrylic particles was 0.5 parts by mass to 10 parts by mass relative to 10 parts by mass of the pigment, the particle size distributions and viscosities of the inks fell within the desired ranges, and the inks were ejected from an inkjet printer stably regardless of the types of the pigments used. On the printed matters produced using the aforementioned inkjet printing inks, the inks were satisfactorily fixed regardless of the types of the substrates.

Example 2

Materials shown in Table 2 were mixed together at compounding compositions shown in Table 2 to prepare yellow inks (inkjet printing inks). The inkjet printing inks thus prepared were evaluated with respect to the jetting stability from an inkjet printer. With respect to skin irritation, the confirmation was carried out in the same manner as in Example 1.

(Jetting Stability)

Each of the resultant color inks was filled in an ink tank in an inkjet printer equipped with an inkjet head LB3 (manufactured by Panasonic precision Device Co., Ltd.). Subsequently, on a piece of inkjet recording paper (thickness: 270 μm) which served as a substrate, a grid-like pattern was formed continuously using each of the inks while changing the printing interval between a point of time immediately after the start of the printing and a point of time at which the next-round printing started, wherein vertical lines and horizontal lines were arranged at 350 μm to 370 μm intervals in the grid-like pattern. Jetting stability was evaluated by observing grid-like patterns recorded on the substrate from 0 minute to 5 minutes of the termination interval. The criteria for the evaluation are the following four ratings:

⊙: a grid-like pattern was formed after 5 minutes;

○: a grid-like pattern was formed after 3 minutes, but was not formed after 5 minutes;

Δ: a grid-like pattern was formed after 0 minute, but was not formed after 3 minutes; and x: no grid-like pattern was formed even after 0 minute.

The results are shown in Table 2.

TABLE 2

|  | Example 2-1 | Example 2-2<br>Yellow ink | Example 2-3 | Comparative<br>Example 2-1 |
|---|---|---|---|---|
| Pigment | Iron oxide yellow: 10% by mass | | | |
| Acrylic particles | 2.5% by mass | | | |
| Alcohol | Glycerin: 10% by mass<br>1,3-propanediol:<br>10% by mass | Glycerin:<br>20% by mass | Glycerin:<br>30% by mass | Glycerin:<br>40% by mass |

TABLE 2-continued

|  | Example 2-1 | Example 2-2 | Example 2-3 | Comparative Example 2-1 |
|---|---|---|---|---|
|  |  | Yellow ink |  |  |
| Water | 67.5% by mass | 67.5% by mass | 57.5% by mass | 47.5% by mass |
| Skin irritation | Irritation was not observed | Irritation was not observed | Irritation was not observed | Irritation was not observed |
| Particle size distribution (nm) | D50: 240<br>D90: 620 | D50: 234<br>D90: 580 | D50: 255<br>D90: 593 | D50: 285<br>D90: 740 |
| Viscosity (mPa · s) | 5.3 | 5.2 | 7.7 | 12.8 |
| Jetting stability | ⊙ | Δ | ○ | X |

(Results)

As shown in Table 2, in the case where the amount of an alcohol was 30% by mass or less relative to the whole amount of each of the inks (Examples 2-1 to 2-3), jetting stability was good. On the contrary, in the case where the amount of an alcohol was more than 30% by mass (Comparative Example 2-1), jetting stability was deteriorated. It is considered that: an ink is hardly dried with the increase in the amount of a trihydric alcohol (glycerin), and consequently the jetting stability of the ink tends to increase; on the contrary, when the amount of an alcohol is excessive, the viscosity of the ink tends to increase, and consequently the viscosity of the ink decreases.

In the case where a trihydric alcohol (glycerin) was combined with a dihydric alcohol, jetting stability was very improved. It is considered that the balance between an ink viscosity and ink drying characteristics was good, and consequently jetting stability was improved.

Example 3

Figure 1A:
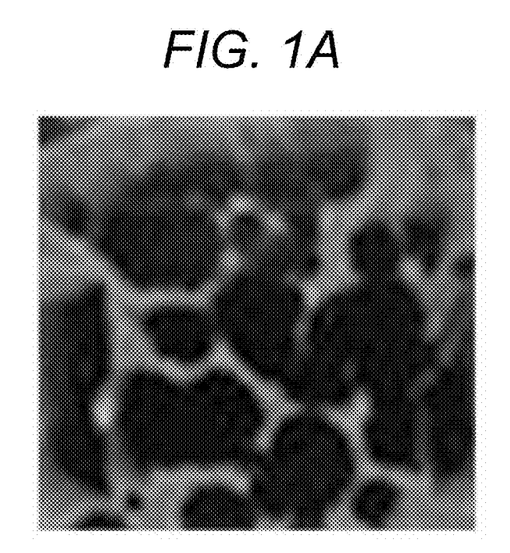
FIG. 1A is a photograph that shows an ink adhesion state of an ink of Comparative Example 3-1 after a ply of tissue paper is pressed against an ink-printed surface subsequent to a fixability test.
Figure 1B:
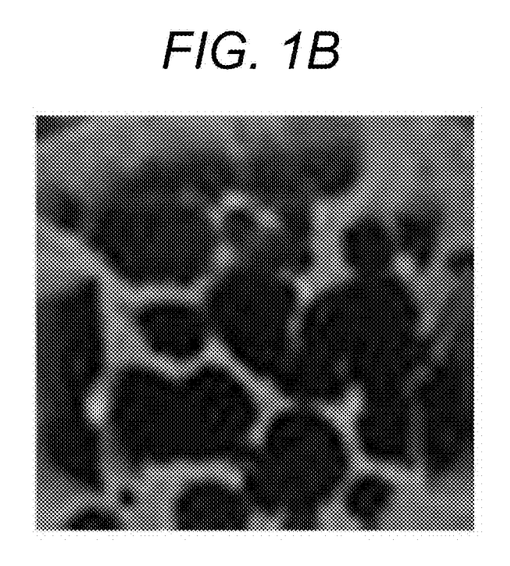
FIG. 1B is a photograph that shows an ink adhesion state of the ink of Comparative Example 3-1 after a ply of tissue paper is pressed against an ink-printed surface subsequent to a water resistance test.
Figure 2A:
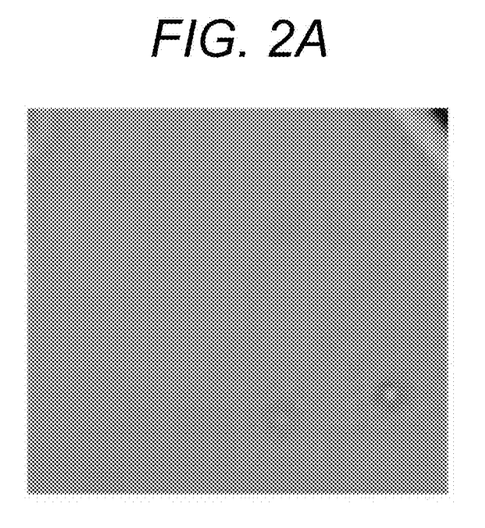
FIG. 2A is a photograph that shows an ink adhesion state of an ink of Comparative Example 3-2 after a ply of tissue paper is pressed against an ink-printed surface subsequent to a fixability test.
Figure 2B:
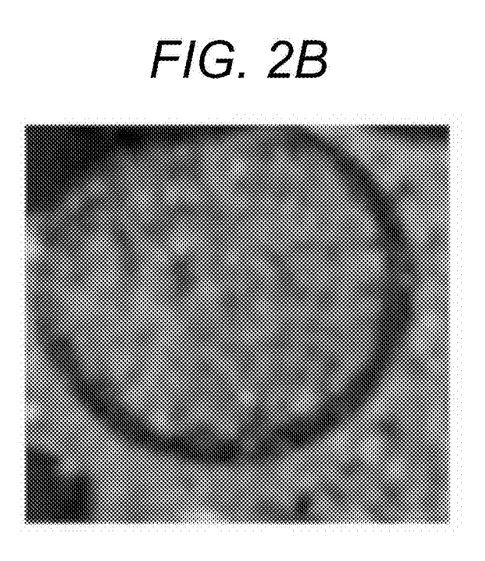
FIG. 2B is a photograph that shows an ink adhesion state of the ink of Comparative Example 3-2 after a ply of tissue paper is pressed against an ink-printed surface subsequent to a water resistance test.
Figure 3A:
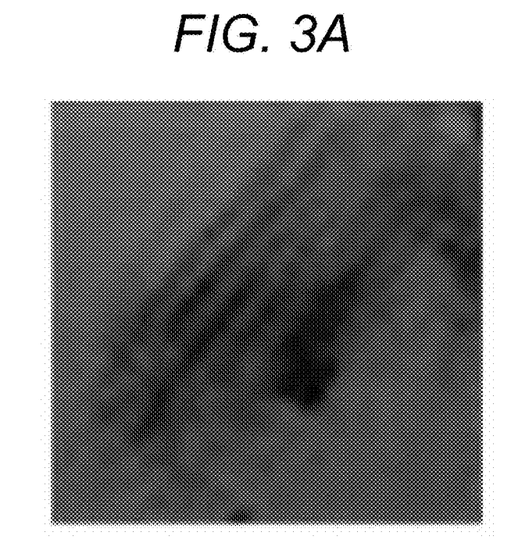
FIG. 3A is a photograph that shows an ink adhesion state of an ink of Comparative Example 3-3 after a ply of tissue paper is pressed against an ink-printed surface subsequent to a fixability test.
Figure 3B:
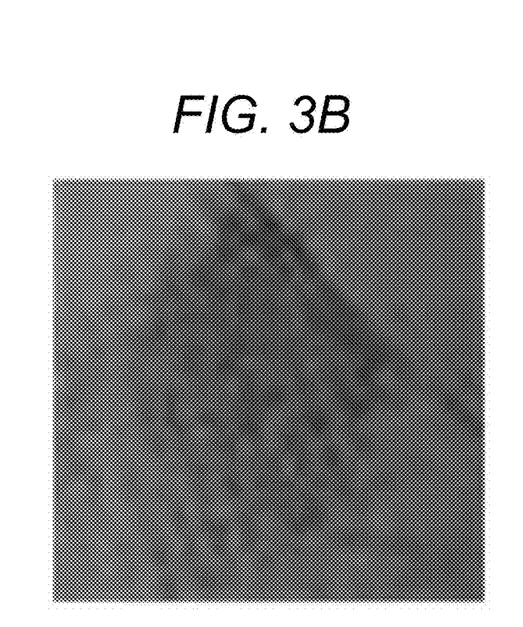
FIG. 3B is a photograph that shows an ink adhesion state of the ink of Comparative Example 3-3 after a ply of tissue paper is pressed against an ink-printed surface subsequent to a water resistance test.
Figure 4A:
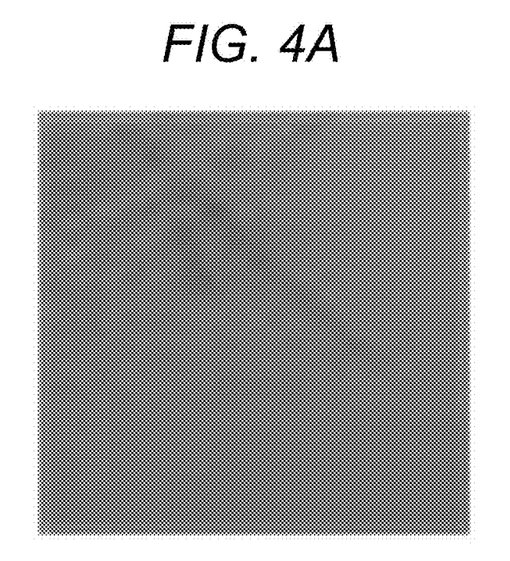
FIG. 4A is a photograph that shows an ink adhesion state of an ink of Example 3-1 after a ply of tissue paper is pressed against an ink-printed surface subsequent to a fixability test.
Figure 4B:
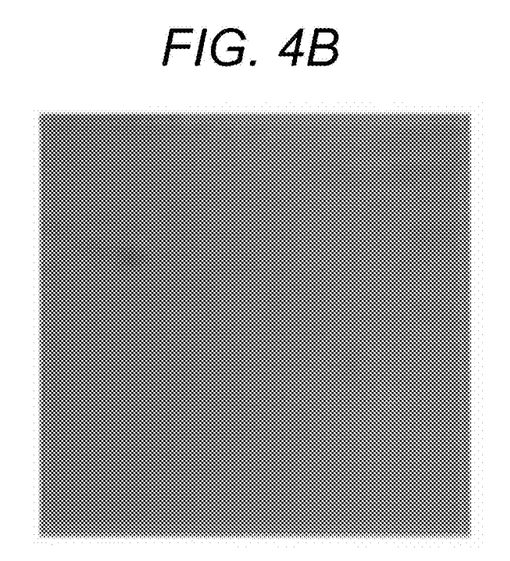
FIG. 4B is a photograph that shows an ink adhesion state of the ink of Example 3-1 after a ply of tissue paper is pressed against an ink-printed surface subsequent to a water resistance test.

Materials shown in Table 3 were mixed together at compounding compositions shown in Table 3 to prepare white inks (inkjet printing inks). The inkjet printing inks thus prepared were evaluated with respect to skin irritation in the same manner as in Example 1. The inks were also evaluated with respect to fixability and water resistance by the below-mentioned methods. The results are shown in Table 3 and FIGS. 1 to 4. FIG. 1A is a photograph that shows an ink adhesion state of an ink of Comparative Example 3-1 after a ply of tissue paper was pressed against an ink-printed surface subsequent to the fixability test, and FIG. 1B is shows an ink adhesion state of an ink of Comparative Example 3-1 after a ply of tissue paper was pressed against an ink-printed surface subsequent to the water resistance test. Likewise, FIGS. 2 to 4 are photographs that respectively show ink adhesion states of inks of Comparative Examples 3-2 and 3-3 and Example 3-1 after a ply of tissue paper was pressed against an ink-printed surface subsequent to the fixability test and the water resistance test.

(Evaluation of Fixability)

In order to make it possible to more easily observe the condition of a coating film after being printed with each of the resultant white inks, each of the inks was applied onto a polyester film, which served as a substrate, by a spin coating method (under the condition where the revolving speed was 2000 rpm) to form a white ink layer on the polyester film. The sheet (i.e., a printed matter) having the white ink layer formed thereon was left at room temperature for 1 hour. A ply of tissue paper was pressed against the white printing layer that had been left, and fixability of the ink was evaluated on the basis of the presence or absence of ink adhesion on the tissue paper.

The criteria for the evaluation were the following two ratings:

○: loss of color was not observed; and
x: loss of color was observed.

(Evaluation of Water Resistance)

In the same manner as in the evaluation of fixability, each of the white inks was applied onto a polyester film by spin coating to produce a printed matter, and the printed matter was left at room temperature for 1 hour. Subsequently, 1 cc of water was dropped onto the white printing layer with a syringe, and then a ply of tissue paper was pressed against the white printing layer. Water resistance of the printed matter was evaluated on the basis of the presence or absence of ink adhesion onto the tissue paper.

The criteria for the evaluation were the following two ratings:

○: loss of color was not observed; and
x: loss of color was observed.

TABLE 3

|  | Comparative Example 3-1 | Comparative Example 3-2 | Comparative Example 3-3 | Example 3-1 |
|---|---|---|---|---|
|  |  | White ink |  |  |
| Pigment | Titanium oxide: 10% by mass | | | |
| Resin | None | Polyvinyl alcohol: 5% by mass | Silicon-based particles: 5% by mass | Acrylic particles: 5% by mass |
| Alcohol | Glycerin: 10% by mass/1,3-propanediol: 10% by mass | | | |
| Water | 70% by mass | 65% by mass | 65% by mass | 65% by mass |
| Skin irritation | Irritation was not observed | Irritation was not observed | Irritation was not observed | Irritation was not observed |
| Fixability | X | ○ | X | ○ |
| Water resistance | X | X | X | ○ |

As shown in Table 3 and FIG. 1 to FIG. 4, in the case where acrylic particles were contained, fixability and water resistance were good (Example 3-1). On the contrary, in the case where each of the inks contained no resin or contained silicon-based particles as a resin, fixability was not improved satisfactorily, loss of ink color in a streak-like shape or a stripe-like shape was observed on a ply of tissue paper when a ply of tissue paper was pressed against an ink-printed surface and, as a matter of course, water resistance had a poor rating (Comparative Examples 3-1 and 3-3). In the case where an ink contained polyvinyl alcohol, even though fixability of the ink was good, loss of ink color was observed when water was dropped, and therefore water resistance was insufficient (Comparative Example 3-2).

Example 4

Materials shown in Table 4 were mixed together at compounding compositions shown in Table 4 to prepare yellow inks (inkjet printing inks). The inkjet printing inks thus prepared were evaluated with respect to skin irritation in the same manner as in Example 1. The inks were also evaluated with respect to fixability and water resistance in the same manner as in Example 3. The results are shown in Table 4.

TABLE 4

|  | Comparative Example 4-1 | Example 4-1 | Example 4-2 | Example 4-3 | Example 4-4 | Comparative Example 4-2 |
|---|---|---|---|---|---|---|
|  |  |  | Yellow ink |  |  |  |
| Pigment | iron oxide yellow: 10% by mass | | | | | |
| Acrylic Particles | None | 1% by mass | 3% by mass | 5% by mass | 10% by mass | 20% by mass |
| Alcohol | Glycerin: 10% by mass/1,3-propanediol: 10% by mass | | | | | |
| Water | 70% by mass | 69% by mass | 67% by mass | 65% by mass | 60% by mass | 50% by mass |
| Skin irritation | Irritation was not observed | Irritation was not observed | Irritation was not observed | Irritation was not observed | Irritation was not observed | Irritation was not observed |
| Fixability | X | ○ | ○ | ○ | ○ | ○ |
| Water resistance | X | ○ | ○ | ○ | ○ | ○ |
| Jetting stability | ⊙ | ⊙ | ⊙ | ⊙ | ○ | Δ |

As shown in Table 4, in the case where acrylic particles were contained as a binder, fixability and water resistance were good (Examples 4-1 to 4-4). On the contrary, in the case where an ink did not contain acrylic particles, ink fixability and water resistance of an image were poor (Comparative Example 4-1). On the other hand, in the case where the amount of acrylic particles was excessive, jetting stability tended to be deteriorated (Comparative Example 4-2).

The inkjet printing ink according to the present disclosure is safe for living bodies, does not cause clogging of a head of an inkjet printer during printing, and therefore has excellent jetting stability. Therefore, the inkjet printing ink can be used for high definition printing on plain paper and dedicated recording paper as well as substrates other than paper such as a plastic material and a cloth. Consequently, the inkjet printing ink is useful as a printing ink for coloring purposes and for the production of packaging containers in medical industries, food industries and cosmetic industries, and others.

What is claimed is:
1. An inkjet printing ink, comprising:
   a pigment in an amount of 3 to 10% by mass, relative to the whole mass of the inkjet printing ink,
   acrylic particles comprising
      homopolymer of an acrylic monomer or
      copolymer consisting of at least two types of acrylic monomers,
   an alcohol, and
   water,
   wherein the alcohol contains a trihydric alcohol in an amount of 10 to 20% by mass relative to the whole amount of the inkjet printing ink, and wherein the alcohol additionally contains a dihydric alcohol selected from the group consisting of
      diethylene glycol,
      propylene glycol,
      1,3-propanediol,
      butylene glycol and
      hexanediol
   in an amount of 10 to 20% by mass relative to the whole amount of the inkjet printing ink,
   a ratio of an amount of the alcohol to a whole mass of the inkjet printing ink is 30% by mass or less, and
   a ratio of an amount of the acrylic particles to a mass of the pigment is 5% by mass to 100% by mass.

2. The inkjet printing ink according to claim 1, wherein the trihydric alcohol is glycerin.

3. The inkjet printing ink according to claim 1, wherein the ratio of the amount the acrylic particles to the mass of the pigment is 15% by mass to 57% by mass.

4. The inkjet printing ink according to claim 1, further comprising at least one selected from the group consisting of a surfactant, a pH adjuster, a thickening agent, an ultraviolet absorber, an ultraviolet scattering agent, an antimicrobial and antifungal agent, a deoxidizing agent, an antioxidant agent, a preservative agent, an antifading agent, an anti-foaming agent, and a fragrance.

5. The inkjet printing ink according to claim 1, wherein the pH value of the inkjet printing ink is 7.0 to 9.5.

6. The inkjet printing ink according to claim 1, wherein the median diameter of the pigment is 10 nm to 300 nm.

7. The inkjet printing ink according to claim 1, wherein the surface tension of the inkjet printing ink at 25° C. is 32 mN/m to 46 mN/m.

8. The inkjet printing ink according to claim 1, wherein the inkjet printing ink is printed on a thin film having a thickness of 10 nm to 1000 nm.

9. The inkjet printing ink according to claim 1, wherein the inkjet printing ink is printed on the surface of a thin film, the thin film having a thickness of 10 nm to 1000 nm and being supported by a material that has water-absorbing properties.

10. The inkjet printing ink according to claim 1, wherein the inkjet printing ink passes a skin irritation test,
   wherein said skin irritation test is carried out on a three-dimensional skin model using a 5% sodium dodecyl sulfate (SDS) solution as an irritation control, and using phosphate buffered saline (PBS) as a negative control, the survival rate of cells in the model is more than 50% after the ink is exposed to the three-dimensional skin model for 18 hours, and subsequently the survival rate of cells in the model is evaluated by a 3-(4,5-dimethyl-2-thiazolyl)-2,5-diphenyl-2H-tetrazolium bromide (MTT) test.

* * * * *